United States Patent [19]

Witter

[11] Patent Number: 4,895,718

[45] Date of Patent: Jan. 23, 1990

[54] SEROTYPE 2 MAREK'S DISEASE VACCINE

[75] Inventor: Richard L. Witter, Okemos, Mich.

[73] Assignee: The United States of America, as represented by the Secretary of Agriculture, Washington, D.C.

[21] Appl. No.: 71,949

[22] Filed: Jul. 10, 1987

[51] Int. Cl.$^4$ .................. A61K 39/12; A61K 37/00; C12N 15/00; C12N 7/08; C12R 1/91
[52] U.S. Cl. ........................................ 424/89; 424/93; 435/172.1; 435/237; 435/948; 935/63; 935/65; 935/70
[58] Field of Search .............. 424/88, 89, 93; 435/68, 435/91, 172.1, 172.3, 235, 236, 237, 240.1, 320; 935/1, 6, 9, 11, 12, 22, 23, 24, 59, 60, 63, 65

[56] References Cited

U.S. PATENT DOCUMENTS 4,160,024 7/1979 Schat et al. ........................ 424/89

OTHER PUBLICATIONS

Paoletti et al (1984), *PNAS*, 81:193.
R. L. Witter, "Characteristics of Marek's Disease Viruses Isolated from Vaccinated Commercial Chicken Flocks: Association of Viral Pathotype with Lymphoma Frequency," Avian Dis. 27(1): 113-132 (Jan.--Mar. 1983).

*Primary Examiner*—Jayme A. Huleatt
*Assistant Examiner*—Richard C. Peet
*Attorney, Agent, or Firm*—M. H. Silverstein; C. P. Ribando; J. D. Fado

[57] ABSTRACT

A serotype 2 Marek's disease vaccine comprising a cloned strain designated as 301B/1 has been derived from a field isolate. This strain is characterized by superior levels of replicative ability and protectivity in chickens as compared to existing commercial serotype 2 strains, and it is virtually nonpathogenic. 301B/1 is particularly useful in the formulation of highly efficacious bivalent and polyvalent vaccines.

6 Claims, No Drawings

SEROTYPE 2 MAREK'S DISEASE VACCINE

BACKGROUND OF THE INVENTION

1. Field of the Invention

Vaccines have been used for the prevention of Marek's disease (MD) in commercial chickens since 1970. There are over 4 billion chickens raised annually in the United States alone. Although vaccination programs have been considered highly effective overall, the poultry industry continues to experience losses due to MD. Given the tendency of MD virus to become more virulent with time coupled with the economic pressures confronting the poultry industry, there is still a strong incentive to develop even more efficacious products that will protect better in the face of early challenge with very virulent field strains. This invention relates to a novel vaccine against MD which does in fact provide superior protection over the existing commercial vaccines.

2. Description of the Prior Art

There are three distinct serotypes of MD virus found in chickens:(1) serotype 1, the oncogenic form responsible for the disease, including high- and low-virulence MD virus and their attenuated variants;(2) serotype 2, a nononcogenic MD virus; and (3) serotype 3, herpesvirus of turkeys (HVT).

The prototype MD vaccine consists of the serotype 3 virus originally isolated from turkeys as reported in Witter et al. I. [Am. J. Vet. Res. 31: 525–538 (1970)]and Okazaki et al., U.S. Patent No. 3,642,574. Its lack of oncogenicity, self-limiting infection, good replication in vivo and in vitro, availability as cell-free and cell-associated preparations, and high protective efficacy have established HVT as a standard for MD vaccines throughout the world. A commonly used strain of HVT is FC126.

Vaccines produced from the naturally avirulent SB-1 strain [Schat et al., J. Natl. Cancer Inst. 60: 1075–1082 (1978) and U.S. Patent No. 4,160,024], an isolate of a serotype 2 MD virus, have been licensed in the United States since 1984. The SB-1 strain is poorly protective against the highly virulent Md5 strain. It is usually used in combination with HVT as a bivalent vaccine since the two viruses together produce greater protection than does either one alone [Schat et al. Avian Pathol. 11: 593–606 (1982); Witter I, Avian Pathol 11: 49–62 (1982)]. This phenomenon has been termed "protective synergism." The SB-1 +HVT bivalent vaccine represents about 18% of the United States market for MD vaccines at present and is considered to be the most efficacious of the various MD products available. However, sporadic losses occur despite its use.

Another MD vaccine produced from strain CVI988 clone C (CVI988/C) has recently been licensed for commercial use in the United States. This vaccine is a mildly virulent serotype 1 MD virus attenuated by serial passage in tissue culture and has been reported by Rispens et al. [Avian Dis. 16: 108–125 (1972)]and deBoer et al. [Avian Dis. 30: 276–283 (1986)].

An experimental vaccine derived from Md11, a very virulent serotype 1 MD field isolate, was reported by Witter I, supra. Md11 was attenuated by 75 serial passages in cell culture, and the resultant vaccine designated Md11/75C. This vaccine has been shown to provide good protection against challenge with Md and most other highly virulent MD viruses tested; but it was less efficacious against challenge with the JM/102W strain, a prototype MD virus effectively protected against by HVT and SB-1 vaccines. Furthermore, its efficacy was consistently lower in chicks with HVT antibody.

Thus, although HVT, SB-1, CVI988/C, and Md11/75C are all effective against certain MD viruses, none of these vaccines protect optimally against all MD challenge viruses in all chickens. In an effort to avert any large-scale outbreaks of MD in the future, the search for improved vaccines has continued.

SUMMARY OF THE INVENTION

I have now discovered a novel MD vaccine derived from a serotype 2 field isolate. The vaccine comprises either a virus cloned from the isolate and having the essential identifying characteristics of the clone designated as 301B/1 or certain derivatives thereof. As compared to other known MD vaccines, 301B/1 provides superior protection, especially when used in combination with HVT. Moreover, this strain appears to be totally nonpathogenic regardless of the maternal antibody status of the chickens.

In accordance with this discovery, it is an object of the invention to provide a novel, totally safe, and highly protective vaccine against MD in chickens.

It is also an object of the invention to provide polyvalent vaccines against MD which are more efficacious than those presently in commercial use.

It is another object of the invention to improve the viability and productivity of chickens, particularly broilers and layers, and to reduce economic losses in the poultry industry caused by MD.

Another object of the invention is to provide an MD vaccine which is characterized by a rapid rate of replication, and thereby enhanced protective efficacy and in vitro production efficiency.

Other objects and advantages of the invention will become readily apparent from the ensuing description.

DETAILED DESCRIPTION OF THE INVENTION

"Vaccine" is defined herein in its broad sense to refer to any type of biological agent in an administratable form capable of stimulating an immune response in an animal inoculated with the vaccine. For purposes of this invention, the vaccine may comprise as the viral agent either the virus itself or an immunogenic (antigenic) component of the virus. The vaccine may also be produced from a vector having inserted therein a gene which encodes an immunogenic component of the subject virus.

Strain 301B/1 is a biological clone of parent strain 301B which was isolated in 1980 from a flock of clinically normal White Leghorn chickens in Borculo, MI, as described by Witter II [Avian Dis. 27(1): 113–132 (1983), herein incorporated by reference]. The 301B/1 clone has been deposited in the American Type Culture Collection in Rockville, MD, and assigned Accession No. ATCC VR2176. Compared to other commercial serotype 2 viruses, such as SB-1, 301B/1 is characterized by superior replicative ability both in vivo and in vitro and also superior protectivity against challenge viruses. Moreover, 301B/1 is virtually nonpathogenic, regardless of the maternal antibody status of the chickens. Contemplated within the scope of this invention are other biological clones or subclones of parent strain 301B which have the essential identifying characteristics of 301B/1. The ensuing discussion relating to 301B/1 is intended to be applicable to such other clones and subclones as well.

Propagation of the 301B/1 virus is readily conducted on a suitable medium such as chicken embryo fibroblasts (CEF). A cell-associated vaccine can be prepared by separation of infected CEF monolayers with trypsin centrifugation, and suspension of the dispersed live cells in cell culture medium or tryptose phosphate broth. To prepare a cell-free virus inoculum, infected cells from the culture are sonicated or otherwise disrupted. The cellular debris is removed by filtration (or centrifugation) and the filtrate (centrifugate) is recovered. It is also contemplated within the scope of the invention to prepare vaccines from the killed virus or from immunogenic components isolated from the virus.

As previously mentioned, the gene or genes encoding the immunogenic component or components responsible for the protective ability of the 301B/1 virus can be inserted into a suitable vector system by recombinant techniques as known in the art. The methodology involving recombinant DNA techniques has now become routine in science and has been successfully demonstrated in analogous applications [E. Paoletti et al., Proc. Natl. Acad. Sci. U.S.A. 81: 193-197 (1984)]. Specifically, the process would first involve the identification of proteins or other components of the virus that are critical to the induction of protective immunity. Next, specific regions of the viral genome (genes) along with any endogenous promoters would be identified and characterized through mapping with restriction endonucleases and determination of the nucleotide sequences. The identified gene or genes would then be spliced into expression vectors such as bacterial plasmids (to produce a killed protein product) or live viruses such as avian herpesviruses or avian poxviruses (to produce a live recombinant DNA vaccine virus). Other types of expression vectors could also be used. Once properly constructed with the necessary promoter sequences, the expression vector will produce the product of the inserted gene; namely, the critical immunizing protein or proteins of the 301B/1. If produced by a vector grown in vitro, the immunizing protein will be obtained from the culture medium, purified, and used with appropriate adjuvants and diluents as a killed vaccine for the immunization of chickens. Other vectors, chosen for their natural infectivity for chickens, will be inoculated directly into chickens as a recombinant live virus vaccine. The vaccine will then produce the immunizing protein in vivo, thus causing protection directly and without the need for additional inoculations.

The viral agent is prepared for administration by formulation in an effective immunization dosage with a pharmaceutically acceptable carrier or diluent, such as physiological saline or tissue culture medium. The expression "effective immunization dosage" is defined as being that amount which will induce immunity in a chicken against challenge by a virulent strain of MD. Immunity is considered as having been induced in a population of chickens when the level of protection for the population is significantly higher than that of an unvaccinated control group. One measure of the level of protection is the protective index (PI), which is calculated as the MD in unvaccinated, MD virus challenged controls minus the MD in vaccinated, MD virus challenged groups and the difference divided by the percent MD in unvaccinated, MD virus challenged controls, with the result multiplied by 100. Typically, the vaccine will contain at least about 1000 PFU (plaque-forming units) of the virus, and preferably between 2000 and 5000 PFU. The vaccine can be effectively administered anytime after the chicken attains immunocompetence, which is at about the 18th day of incubation (3 days prehatch); but it is normally administered by inoculation within 24-48 hr after hatching.

Appropriate adjuvants as known in the art may also be included in the vaccine formulation. In many cases, the vaccinal efficacy can be enhanced by combining the 301B/1 with HVT or other viral agents into bivalent or polyvalent vaccines.

The following examples are intended only to further illustrate the invention and are not intended to limit the scope of the invention which is defined by the claims.

EXAMPLE 1

Field isolate 301B as reported in Witter II, supra, was cloned using cell-free virus inocula obtained from sonicated CEF cell cultures inoculated with 301B at the fifth passage. A plaque isolated from the initial cloning was then serially passaged on CEF and a seed stock was preserved at the 11th passage through cryopreservation. Infected monolayer cultures dispersed with trypsin were centrifuged and suspended in tissue culture medium containing 10% dimethylsulfoxide and 10% calf serum. This live cell suspension was slow frozen at about 1° C. per min and stored in a liquid nitrogen freezer at about $-196°$ C. Subsequent viral stocks were prepared by serial propagation of the 11th passage seed stock on CEF. Stocks at passages 11-13 were used in experiments. Currently available working stocks are at passage 14; one of the 14th passage working stocks designated 301B/1 corresponds to ATCC VR2176, previously mentioned. Titers of viral stocks are usually about $1 \times 10^6$ PFU/ml.

EXAMPLE 2

This experiment was designed to compare the long-term pathogenicity of 301B/1 in chickens with and without maternal antibodies. The pathogenicity tests were conducted on maternal antibody negative (ab—) chickens. These were $F_1$ progeny of line $15I_5$ males and line $7_1$ females that received no vaccinations and were held in positive pressure, flexible canopy isolators as part of the laboratory specific pathogen-free flock. These breeders were free of antibodies to MD virus, HVT, avian leukosis virus, reticuloendotheliosis virus, and other common poultry pathogens.

Groups of 40 ab—chickens were inoculated with 20,000 PFU of 301B/1 or SB- 1 at 1 day posthatch by the intraabdominal route. A group of 40 ab—chickens was similarly inoculated with 1000 PFU of Md5, and a control group received no inoculation at all. Each group was held in separate plastic canopy positive pressure isolators for about 17 wks. At termination all birds were weighed and necropsied. The body weights were adjusted for sex differences by multiplying female weights by a factor computed by dividing the mean of all male weights by the mean of all female weights. The results are reported in Table I below.

EXAMPLE 3

To test for the rate of contact transmission of the 301B/1 clone of Example 1 as compared to other viruses, uninoculated chickens (ab—) were intermingled with groups of 30 other chickens of Example 2 which had been inoculated with 20,00PFU of virus. At 10 wks of age, the uninoculated birds were removed and bled. Viruses were isolated from the sera by standard methods. Antibodies were detected in sera by the agar gel precipitin test using an antigen prepared from the feather tips of chickens infected with a virulent serotype 1 MD viral isolate. The results reported in Table II below indicate that all birds exposed by contact to 301B/1, SB-1, and Md5 became infected.

EXAMPLE 4

Chickens from each of the groups in Example 2 vaccinated with 301B/1 and SB-1 were bled at termination (17 wks) and tested for viremia persistence. Buffy coat cells were assayed for virus by standard procedures on CEF or DEF cultures.

TABLE I

| | | | | MD lesions | | |
|---|---|---|---|---|---|---|
| Chicken type | Vaccine | PFU dose | No. birds | % Mort | % Gross[a] | Body weights[b] |
| 15 × 7 ab- | 301B/1 | 20,000 | 39 | 0.0 | 0.0 | 1554.3 |
| | SB-1 | 20,000 | 40 | 0.0 | 0.0 | 1563.4 |
| | Md5 | 1,000 | 39 | 100.00 | 100.0 | — |
| | None | 0 | 38 | 0.0 | 0.0 | 1543.3 |

Long-Term Pathogenicity Test of Vaccin Viruses

[a]Includes mortality.
[b]Means do not differ (p < 0.05) by Bonferroni t-tests.

TABLE II

Evaluation of Vaccine Viruses for Transmission by Direct Contact

| | Transmission frequency | |
|---|---|---|
| Virus | Virus isolation | Antibody |
| 301B-1 | 2/5 (5.7)[a] | 5/5 |
| SB-1 | 5/6 (3.0) | 6/6 |
| Md5 | 2/2 (43.2) | 2/2 |
| None | 0/6 | 0/6 |

[a]Mean PFU isolated per 2 × 10[6] buffy coat cells in parenthesis.

The results reported in Table III below indicate that the tested vaccines were equally effective in inducing viremias.

EXAMPLE 5

The protectivity against challenge strains of MD for clone 301B/1 was compared to that of JM/102W/48 (serotype 1), an attenuated strain of JM/102W as described by Witter et al. III [J. Natl. Cancer Inst. 62: 143-151 (1979)]and of three different passage levels of strain SB-1/1 (serotype 2).

Protection tests utilized groups of ab+F$_1$ progeny from breeders (15I$_5$ males ×7$_1$ femalesl) vaccinated with vaccine viruses of all three serotypes, i.e., Md11/75C (serotype 1), SB-1 (serotype 2), and FC126 (serotype 3), at a dose of 1000 PFU for each virus. Sera were obtained from these breeder flocks at several intervals during lay and tested for MD antibodies. The flocks were held in isolation pens and were not intentionally exposed to virulent serotype 1 viruses.

TABLE III

Viremia Persistence 17 Weeks After Inoculation with Vaccine Viruses

| | PFU | Virus isolation | |
|---|---|---|---|
| Virus | dose | +/Total | Mean PFU[a] |
| 301B/1 | 20,000 | 12/12 | 24.0 |
| SB-1 | 20,000 | 12/12 | 25.8 |

[a]Per 2 × 10[6] buffy coat cells. Means do not differ (P < 0.05) by Bonferroni t-tests.

The test chickens were inoculated by the intraabdominal route at 1-day posthatch with 2000 PFU of appropriate vaccines. Challenge was done 5 days post vaccination with inoculum administered intraabdominally at a dose of 500 PFU per chick. The groups were held for about 56 days post challenge, killed, necropsied, and the presence of gross MD lesions recorded. Birds dying during the experiment were examined for gross lesions. The birds considered to be at risk were those positive for MD lesions plus those survivors without lesions.

The protective efficacy of each virus was evaluated against challenge with JM/102W and Md5 in two different trials, each using 20 birds per group. In a third trial, each virus was used with FC126 as a bivalent vaccine and challenged with a mixture of virulent viruses using 40 birds per group; protection was compared to that provided by the FC126 vaccine included as an internal control in each experiment. A protective index was calculated as the percent MD in unvaccinated, challenged controls minus the percent MD in vaccinated, challenged groups divided by the percent MD in unvaccinated, challenged controls multiplied by 100. The results are reported in Table IV below. It is apparent that the 301B/1 virus provided excellent protection alone against JM/102W and Md5 challenge and, at least in one trial, significantly augmented the protective efficacy of FC126.

TABLE IV

| | | | Protective Efficacy | | | | | | |
|---|---|---|---|---|---|---|---|---|---|
| | | | Protection vs. JM/102W | | Protection vs. Md5 | | Augmentation of HVT protection[a] | | |
| Serotype | Virus strain | Passage | PI | Compare vs. HVT PI | PI | Compare vs. HVT PI | PI | % of HVT PI | Compare vs. HVT |
| 1 | JM/102W/48 | 48 | 31 | —[b] | 52 | ns[b] | 49 | 114 | ns[b] |
| 2 | 301B/1 | 11 | [100][c] | ns | [44] | ns | [67] | 186 | + |
| 2 | SB-1/1 | 23 | 93 | ns | 57 | ns | 53 | 136 | ns |
| 2 | SB-1/1 | 64 | 69 | ns | 0 | — | 30 | 136 | ns |
| 2 | SB-1/1 | 98 | 38 | — | 1 | — | 26 | 118 | ns |

Abbreviations: PI = protective index; HVT = FC126 strain of turkey herpesvirus.
[a]Challenged with a mixture of JM/102W, Md5, and 287L; 1000 PFU aggregate dose.
[b]Results of Chi-square analysis: ns = not significant (P > 0.05); + = PI greater than HVT control (P < 0.05); — = PI less than HVT control (P < 0.05); nd = not analyzed because data from internal HVT control was not available.
[c][ ] = PI values of viruses selected for further analysis as the best representitatives of their class.

EXAMPLE 6

The protective efficacy of clone 301B/1 was compared in a series of protection trials to commercial and other experimental vaccines. Vaccine Md11/75C/R2 is the subject of commonly assigned copending application Ser. No. 07/71,948, filed on July 10, 1987. These trials were conducted essentially as described in Example 5, except as noted below. The dose for polyvalent vaccines was the same in aggregate (2000 PFU) as for monovalent vaccines, with each constituent virus equally represented. In the first series (Trials 1-4), 14 vaccines were evaluated including six monovalent, seven bivalent, and one trivalent products. Control groups either received a placebo consisting of normal CEF at a concentration equivalent to that of other vaccines or were nonvaccinated. Chickens in each trial were challenged with a different virulent or very virulent serotype 1 MD virus; Md5, RB1B, 287L, and 295. In the second series (Trials 5-8), the number of vaccines was reduced to nine but otherwise was identical to the first series. In the third series (Trials 9-12), the same nine vaccines were evaluated but the trials had slightly different designs: chickens in Trials 9 and 10 were challenged with Md5 but at 1 day by contact, or at 11 days by inoculation. Trial 11 utilized a commercial White Leghorn chicken strain with Md5 challenge at 5 days post vaccination. Trial 12 differed from the others because only five vaccines were tested, groups contained 40 chickens, and the experimental period was 17 wks post challenge.

There was close agreement in the results of the various series. Although each experiment was not a direct replicate, the similarity in design and the comparability of results permitted consolidation of the results into Table V below. As a monovalent vaccine, 301B/1 was at least equal to FC126, SB-1, and CVI988/C. However, 301B/1 was particularly effective in augmenting the protective efficacy of FC126.

TABLE V

| | Statistical Analysis of Vaccine Efficacy | | | | | | |
|---|---|---|---|---|---|---|---|
| | | Mean PI | Greater than$^a$ | | | | |
| Vaccine | MD+/Total | ±SEM | HVT | BiV | CVI | SB-1 | None |
| FC126 | 140/213 | 30.4 ± 4.7 | — | — | — | — | ABC |
| SB-1 | 135/217 | 33.7 ± 4.1 | — | — | — | — | ABC |
| 301B/1 | 120/214 | 40.2 ± 5.9 | — | — | B | — | ABC |
| CVI988/C | 147/212 | 26.2 ± 4.7 | — | — | — | — | ABC |
| Md11/75C/R2 | 79/212 | 60.1 ± 7.1 | ABC | — | ABC | ABC | ABC |
| FC126 + SB-1 | 85/216 | 58.6 ± 5.2 | ABC | — | ABC | ABC | ABC |
| FC126 + 301B/1 | 55/207 | 71.6 ± 4.4 | ABC | AB | ABC | ABC | ABC |
| FC126 + SB-1 + Md11/75C/R2 | 56/213 | 72.6 ± 4.5 | ABC | AB | ABC | ABC | ABC |
| FC126 + 301B/1 + Md11/75C/R2 | 19/138 | 85.6 ± 3.8$^b$ | ABC | AB | ABC | ABC | ABC |
| None | 196/209 | — | | | | | |

Abbreviations: MD + = birds positive for Marek's disease lesions; PI = protective index; SEM = standard error of the mean; HVT = FC126 strain of turkey herpesvirus; BiV = bivalent (FC126 + SB-1) vaccine; CVI = CVI988/C.
$^a$Statistical analysis by three methods: A = Vaccine PI greater (P < 0.05) than indicated vaccine by Youden index analyses; B = Vaccine PI greater (P < 0.05) than indicated vaccine by Chi-square analyses; C = Vaccine PI greater (P < 0.05) than indicated vaccine by Bonferroni t-tests.
$^b$Analyzed separately on basis of data from Trials 5-11.

The bivalent 301B/1 +FC126 vaccine protected 72.0% of chickens in 11 trials, and was superior to FC126 alone (30.3% protection) and to bivalent SB-1 +FC126 (58.5% protection). The trivalent composed of FC126 +301B/1 +Md11/75C/R2 consistently provided the best protection of any vaccine (mean protection 85.6%, range 65-100%) and ranked first in five of eight trials.

Data from Trials 1-11 were used to compare paired protection data from the two serotype 2 viruses, 301B/1 and SB-1. A paired comparison represents data from two lots in the same trial where treatment variables were identical except for the use of the indicated viruses as the vaccines (Table VI). These analyses indicate that 301B/1 had a higher mean protective index than SB-1. Also, 301B/1 performed better than SB-1 in a significantly greater number of comparisons than SB-1 outperformed 301B/1.

EXAMPLE 7

Viruses were tested for growth rate at 3 days post inoculation and plaque size at 5 days post inoculation in CEF cultures as previously described by Witter et al. IV [Avian Dis. 24: 210-232 (1980)]. Fifteen plaques were measured for each virus. To determine cell-free virus production, CEF cultures were inoculated with high doses of cell-associated virus and harvested by trypsinization 2 to 3 days post inoculation when cytopathic effects were maximum. One portion of the culture was assayed for cell-associated virus in the usual way. The other portion was suspended in SPGA buffer, sonicated for 60 sec in three 20-sec thrusts at a power setting of 100 w with a "Braun-sonic" 1510 sonifier, and centrifuged at 15,600 ×g for 3 min. The top one-half of the supernatant was carefully removed, diluted in SPGA buffer, and assayed by inoculation of drained CEF monolayer cultures. After absorption for 20 min at 38° C., growth medium was added and the cultures maintained under standard conditions until plaques could be enumerated. The data are expressed as the number of cell-free PFU recovered per 10$^6$ cell-associated PFU. The results are reported in Table VII below. As measured by 3-day growth rates, 301B/1 grew twice as fast as SB-1 and was comparable in terms of plaque size and cell-free virus production.

It is understood that the foregoing detailed description is given merely by way of illustration and that modification and variations may be made therein without departing from the spirit and scope of the invention.

TABLE VI

| Analysis of Paired Comparisons in Eleven Trials | | | | |
|---|---|---|---|---|
| | Total | | Comparisons$^b$ | |
| Vaccine | pairs | Mean PI$^a$ | Greater | Equal |
| 301B/1 | 29 | 63.4$^A$ | 20$^A$ | 3 |
| SB-1 | 29 | 52.9$^A$ | 6$^B$ | 3 |

$^a$Mean protective index values with different superscripts within the same pair group are different (P < 0.05) by Bonferroni t-tests.
$^b$Number of paired comparisons in which the PI of the designated virus was greater, lesser, or equal to the alternate virus. Values with different superscripts are different (P < 0.05) by Chi-square analysis.

TABLE VII

| Growth Characteristics of Vaccine Viruses in CEF Cultures | | | |
|---|---|---|---|
| Virus | Growth rate$^a$ | Plaque size$^b$ | Cell-free virus production$^c$ |
| 301B/1 | 33.0 | 0.028$^A$ | 86 |
| SB-1 | 14.7 | 0.022$^A$ | 77 |

TABLE VII-continued

Growth Characteristics of Vaccine Viruses in CEF Cultures

| Virus | Growth rate[a] | Plaque size[b] | Cell-free virus production[c] |
| --- | --- | --- | --- |
| CVI988/C | 53.7 | 0.125[B] | 8 |

[a]Number of PFU per input PFU 3 days after innoculation.
[b]Mean area in mm$^2$ of 15 virus plaques measured 5 days after innoculation. Means with different superscripts are different ($P < 0.05$) by Bonferroni t-tests.
[c]Number of cell free PFU recovered 2-3 days after innoculation per $10^6$ cell-associated PFU.

I claim:

1. A vaccine comprising: (1) in an effective immunization dosage a viral agent, wherein said viral agent is a cloned virus having the essential identifying characteristics of 301B/1, and (2) a pharmaceutically acceptable carrier or diluent.

2. The vaccine of claim 1 further comprising a second viral agent which is of the HVT type.

3. The vaccine of claim 1 wherein said virus is live as a cell-associated preparation.

4. A method of protecting a chicken against Marek's disease comprising inoculating said chicken with a vaccine comprising an effective immunization dosage of a viral agent, wherein said viral agent is a cloned virus having the essential identifying characteristics of 301B/1.

5. The method of claim 4 wherein said vaccine further comprises a second viral agent which is of the HVT type.

6. The method of claim 4 wherein said virus is live as a cell-associated preparation.

* * * * *